(12) United States Patent
Bolognia et al.

(10) Patent No.: US 11,587,839 B2
(45) Date of Patent: Feb. 21, 2023

(54) DEVICE WITH CHEMICAL REACTION CHAMBER

(71) Applicant: Analog Devices, Inc., Norwood, MA (US)

(72) Inventors: David Frank Bolognia, Charlestown, MA (US); Brian Hall, North Andover, MA (US)

(73) Assignee: Analog Devices, Inc., Wilmington, MA (US)

( * ) Notice: Subject to any disclaimer, the term of this patent is extended or adjusted under 35 U.S.C. 154(b) by 0 days.

(21) Appl. No.: 16/859,665

(22) Filed: Apr. 27, 2020

(65) Prior Publication Data

US 2020/0411398 A1 Dec. 31, 2020

Related U.S. Application Data

(60) Provisional application No. 62/867,703, filed on Jun. 27, 2019.

(51) Int. Cl.
*H01L 23/20* (2006.01)
*H01L 23/495* (2006.01)
*C25B 9/63* (2021.01)

(52) U.S. Cl.
CPC .............. *H01L 23/20* (2013.01); *C25B 9/63* (2021.01); *H01L 23/49558* (2013.01)

(58) Field of Classification Search
None
See application file for complete search history.

(56) References Cited

U.S. PATENT DOCUMENTS

| 2,729,976 | A | 1/1956 | Laub |
| 4,335,835 | A | 6/1982 | Beigler et al. |
| 4,575,330 | A | 3/1986 | Hull |
| 4,587,843 | A | 5/1986 | Tokura et al. |
| 4,671,852 | A | 6/1987 | Pyke |
| 4,688,424 | A | 8/1987 | Handtmann et al. |
| 4,752,352 | A | 6/1988 | Feygin |
| 4,863,538 | A | 9/1989 | Deckard |

(Continued)

FOREIGN PATENT DOCUMENTS

| CN | 1728365 A | 2/2006 |
| CN | 1877989 | 12/2006 |

(Continued)

OTHER PUBLICATIONS

Chait et al. "Custom Designed Microstructures Using Metamaterials," Antenna Systems & Technology Magazine and Conference, World Wide Web Address: antennasonline.com/eprints/EoPlex_Sept10.html; accessed Aug. 24, 2012.

(Continued)

*Primary Examiner* — Bo B Jang
(74) *Attorney, Agent, or Firm* — Knobbe, Martens, Olson & Bear, LLP

(57) ABSTRACT

A device is disclosed. The device includes a housing that defines a chamber. The chamber is to be at least partially filled with an electrolyte material. The device also includes a plurality of electrodes that are at least partially embedded in the housing and exposed to the chamber. The device further includes an access port that provides fluid communication between an interior of the housing and the outside environs.

20 Claims, 12 Drawing Sheets

(56) References Cited

U.S. PATENT DOCUMENTS

| | | |
|---|---|---|
| 5,073,094 A | 12/1991 | Dorman et al. |
| 5,173,166 A | 12/1992 | Tomantschger et al. |
| 5,183,550 A | 2/1993 | Mattiessen |
| 5,222,395 A | 6/1993 | Matubara et al. |
| 5,313,365 A | 5/1994 | Pennisi et al. |
| 5,348,693 A | 9/1994 | Taylor et al. |
| 5,527,288 A | 6/1996 | Gross et al. |
| 5,650,593 A * | 7/1997 | McMillan ............... H01L 23/04 174/542 |
| 5,666,127 A | 9/1997 | Kochiyama et al. |
| 5,792,952 A | 8/1998 | Ritchart |
| 5,831,159 A | 11/1998 | Renger |
| 5,870,482 A | 2/1999 | Loeppert et al. |
| 6,075,239 A | 6/2000 | Aksyuk et al. |
| 6,537,437 B1 | 3/2003 | Galambos et al. |
| 6,607,495 B1 | 8/2003 | Shalak et al. |
| 6,699,234 B2 | 3/2004 | Yeh |
| 6,765,287 B1 | 7/2004 | Lin |
| 6,781,231 B2 | 8/2004 | Minervini |
| 6,800,930 B2 | 10/2004 | Jackson et al. |
| 6,803,559 B2 | 10/2004 | Hsu et al. |
| 6,864,564 B2 * | 3/2005 | Ke ..................... H01L 23/057 257/666 |
| 6,879,429 B2 | 4/2005 | Wong et al. |
| 6,889,559 B2 | 5/2005 | Gimson |
| 6,894,502 B2 | 5/2005 | Feng et al. |
| 6,997,698 B2 | 2/2006 | Silverbrook |
| 7,060,530 B2 * | 6/2006 | Kanatake ............... H01L 21/50 438/112 |
| 7,077,938 B1 | 7/2006 | Austen et al. |
| 7,130,177 B2 | 10/2006 | Aizawa et al. |
| 7,202,552 B2 | 4/2007 | Zhe et al. |
| 7,208,832 B2 | 4/2007 | Yamagata |
| 7,242,089 B2 | 7/2007 | Minervini |
| 7,255,551 B2 | 8/2007 | Taylor et al. |
| D575,056 S | 8/2008 | Tan |
| 7,550,834 B2 | 6/2009 | Yu et al. |
| 7,648,911 B2 | 1/2010 | Pagaila et al. |
| 7,691,747 B2 | 4/2010 | Lin et al. |
| 7,719,427 B2 | 5/2010 | Hsiung et al. |
| 7,723,831 B2 | 5/2010 | Kwang et al. |
| 7,855,429 B2 | 12/2010 | Ishida et al. |
| 7,875,942 B2 | 1/2011 | Cortese et al. |
| 7,898,043 B2 | 3/2011 | Ziglioli et al. |
| 8,044,418 B2 * | 10/2011 | Loh ....................... H01L 33/642 257/98 |
| 8,101,898 B2 | 1/2012 | Koste et al. |
| 8,115,283 B1 | 2/2012 | Bolognia et al. |
| 8,155,355 B2 | 4/2012 | Ogura et al. |
| 8,199,939 B2 | 6/2012 | Suvanto et al. |
| 8,274,147 B2 | 9/2012 | Rofougaran et al. |
| 8,280,207 B2 | 10/2012 | Pinguet et al. |
| 8,300,870 B2 | 10/2012 | Lee et al. |
| 8,339,798 B2 | 12/2012 | Minoo et al. |
| 8,350,382 B2 | 1/2013 | Furgut et al. |
| 8,362,589 B2 | 1/2013 | Quinn |
| 8,368,654 B2 | 2/2013 | Rosenblatt et al. |
| 8,390,083 B2 | 3/2013 | O'Donnell et al. |
| 8,395,252 B1 | 3/2013 | Yang |
| 8,402,666 B1 | 3/2013 | Hsu et al. |
| 8,436,690 B2 | 5/2013 | McCraith et al. |
| 8,436,698 B2 | 5/2013 | Rogers |
| 8,502,329 B2 | 8/2013 | Hsieh et al. |
| 8,569,861 B2 | 10/2013 | O'Donnell et al. |
| 8,574,413 B2 | 11/2013 | Mosley et al. |
| 8,577,063 B2 | 11/2013 | Yang |
| 8,625,832 B2 | 1/2014 | Lillelund |
| 8,637,943 B1 | 1/2014 | Yang |
| 8,754,643 B2 | 6/2014 | Gugel et al. |
| 8,779,532 B2 | 7/2014 | O'Donnell et al. |
| 8,847,340 B2 | 9/2014 | Baldo et al. |
| 8,852,513 B1 | 10/2014 | Speer et al. |
| 8,853,799 B2 | 10/2014 | O'Donnell et al. |
| 8,890,285 B2 | 11/2014 | O'Donnell et al. |
| 8,890,286 B2 | 11/2014 | O'Donnell et al. |
| 8,920,376 B2 * | 12/2014 | Caffey ............... A61M 5/14526 604/141 |
| 8,939,930 B2 * | 1/2015 | Li ........................ A61M 5/155 604/67 |
| 8,957,497 B2 | 2/2015 | O'Donnell et al. |
| 9,027,400 B2 * | 5/2015 | Le Neel ............... G01N 27/223 73/335.04 |
| 9,041,150 B2 | 5/2015 | O'Donnell et al. |
| 9,063,084 B1 | 6/2015 | Lin et al. |
| 9,132,231 B2 | 9/2015 | Gross et al. |
| 9,156,680 B2 | 10/2015 | Kierse et al. |
| 9,267,915 B2 | 2/2016 | O'Donnell et al. |
| 9,269,831 B2 | 2/2016 | Ehrenpfordt et al. |
| 9,492,614 B2 | 11/2016 | Kamen et al. |
| 9,545,669 B2 | 1/2017 | Åklint et al. |
| 9,550,023 B2 * | 1/2017 | Pang ................... F04B 43/0054 |
| 9,616,171 B2 | 4/2017 | Qin et al. |
| 9,618,490 B2 | 4/2017 | Paik et al. |
| 9,661,408 B2 | 5/2017 | Kierse et al. |
| 9,818,665 B2 | 11/2017 | Elian et al. |
| 9,983,164 B1 | 5/2018 | Allen et al. |
| 9,993,982 B2 | 6/2018 | Sherrer et al. |
| 10,398,832 B2 * | 9/2019 | Qin ..................... B81C 1/00158 |
| 10,730,743 B2 * | 8/2020 | Kierse ................. G01N 27/404 |
| 2002/0133120 A1 * | 9/2002 | Yeh .................... A61M 5/14248 604/131 |
| 2002/0163066 A1 * | 11/2002 | Ke ..................... H01L 23/49541 257/678 |
| 2002/0190266 A1 * | 12/2002 | Kanatake ............... H01L 23/10 257/112 |
| 2004/0000713 A1 | 1/2004 | Yamashita et al. |
| 2004/0149027 A1 * | 8/2004 | Gimson ................. G01F 1/6842 73/204.11 |
| 2004/0190254 A1 | 9/2004 | Hu et al. |
| 2005/0156584 A1 | 7/2005 | Feng |
| 2005/0189622 A1 | 9/2005 | Humpston et al. |
| 2005/0253244 A1 | 11/2005 | Chang |
| 2006/0139883 A1 | 6/2006 | Hu et al. |
| 2006/0258053 A1 | 11/2006 | Lee et al. |
| 2006/0261460 A1 | 11/2006 | Sato et al. |
| 2006/0266098 A1 | 11/2006 | Eickhoff et al. |
| 2006/0283252 A1 | 12/2006 | Liu et al. |
| 2007/0053504 A1 | 3/2007 | Sato et al. |
| 2007/0071268 A1 | 3/2007 | Harney et al. |
| 2007/0082421 A1 | 4/2007 | Minerviani |
| 2007/0138027 A1 | 6/2007 | Dinsmoor et al. |
| 2007/0187826 A1 | 8/2007 | Shim et al. |
| 2007/0202627 A1 | 8/2007 | Minervini |
| 2007/0210423 A1 | 9/2007 | Hsu |
| 2007/0246806 A1 | 10/2007 | Ong et al. |
| 2007/0246813 A1 | 10/2007 | Ong et al. |
| 2007/0278601 A1 | 12/2007 | Goodelle et al. |
| 2007/0296065 A1 | 12/2007 | Yew et al. |
| 2008/0012036 A1 * | 1/2008 | Loh ....................... H01L 33/642 257/99 |
| 2008/0054431 A1 | 3/2008 | Wang et al. |
| 2008/0075309 A1 | 3/2008 | Chen et al. |
| 2008/0079142 A1 | 4/2008 | Carmona et al. |
| 2008/0151590 A1 | 6/2008 | Rogers et al. |
| 2008/0175425 A1 | 7/2008 | Roberts et al. |
| 2008/0217766 A1 | 9/2008 | Minervini |
| 2008/0234599 A1 | 9/2008 | Chiao et al. |
| 2008/0265421 A1 | 10/2008 | Brunnbauer et al. |
| 2008/0304681 A1 | 12/2008 | Langlois et al. |
| 2009/0008792 A1 | 1/2009 | Ko et al. |
| 2009/0029492 A1 | 1/2009 | Tu et al. |
| 2009/0039492 A1 | 2/2009 | Kang et al. |
| 2009/0072334 A1 | 3/2009 | Saitoh |
| 2009/0079065 A1 | 3/2009 | Furgut et al. |
| 2009/0170242 A1 | 7/2009 | Lin et al. |
| 2009/0194829 A1 | 8/2009 | Chung et al. |
| 2009/0200620 A1 | 8/2009 | Omura et al. |
| 2009/0202089 A1 | 8/2009 | Zhang et al. |
| 2009/0204250 A1 | 8/2009 | Potyrailo et al. |
| 2009/0261460 A1 | 10/2009 | Kuan et al. |
| 2009/0283871 A1 | 11/2009 | Chang et al. |
| 2009/0302437 A1 | 12/2009 | Kim et al. |
| 2009/0320698 A1 | 12/2009 | LaPerna Wong |

(56) References Cited

U.S. PATENT DOCUMENTS

| | | |
|---|---|---|
| 2009/0321930 A1 | 12/2009 | Marcoux |
| 2010/0009133 A1 | 1/2010 | Chait |
| 2010/0032748 A1 | 2/2010 | Edwards |
| 2010/0044704 A1 | 2/2010 | Male et al. |
| 2010/0052630 A1 | 3/2010 | Chen |
| 2010/0055895 A1 | 3/2010 | Zafiropoulo et al. |
| 2010/0086146 A1 | 4/2010 | Gong et al. |
| 2010/0090295 A1 | 4/2010 | Zhe et al. |
| 2010/0134139 A1 | 6/2010 | Chen et al. |
| 2010/0142744 A1 | 6/2010 | Rombach et al. |
| 2010/0155863 A1 | 6/2010 | Weekamp |
| 2010/0171203 A1 | 7/2010 | Chen et al. |
| 2010/0181643 A1 | 7/2010 | Kothandaraman et al. |
| 2010/0193905 A1 | 8/2010 | Kim et al. |
| 2010/0284553 A1 | 11/2010 | Conti et al. |
| 2011/0013787 A1 | 1/2011 | Chang |
| 2011/0023929 A1 | 2/2011 | Edwards |
| 2011/0057273 A1 | 3/2011 | O'Donnell et al. |
| 2011/0060280 A1 | 3/2011 | Caffey et al. |
| 2011/0101537 A1 | 5/2011 | Barth |
| 2011/0108933 A1 | 5/2011 | Nakatani |
| 2011/0140703 A1 | 6/2011 | Chiao et al. |
| 2011/0198714 A1 | 8/2011 | Yang |
| 2011/0199057 A1 | 8/2011 | Ivanov et al. |
| 2011/0270188 A1* | 11/2011 | Caffey .............. A61M 5/14593 604/151 |
| 2011/0293126 A1 | 12/2011 | Maekawa et al. |
| 2011/0317863 A1 | 12/2011 | Inoda et al. |
| 2012/0065617 A1 | 3/2012 | Matsiev et al. |
| 2012/0237073 A1 | 9/2012 | Goida et al. |
| 2012/0250925 A1 | 10/2012 | Lillelund |
| 2012/0321111 A1 | 12/2012 | Lillelund |
| 2013/0012873 A1* | 1/2013 | Gross .................... A61M 5/155 604/143 |
| 2013/0037909 A1 | 2/2013 | French |
| 2013/0105952 A1 | 5/2013 | Fontana et al. |
| 2013/0119509 A1 | 5/2013 | Farooq et al. |
| 2013/0139587 A1* | 6/2013 | Le Neel ............... G01N 27/223 73/335.04 |
| 2013/0178792 A1* | 7/2013 | Li ..................... A61M 5/14566 604/67 |
| 2013/0178826 A1* | 7/2013 | Li ......................... A61M 5/155 604/506 |
| 2013/0184640 A1* | 7/2013 | Li ..................... A61M 5/14526 604/67 |
| 2013/0184641 A1* | 7/2013 | Li ..................... A61M 5/16854 604/67 |
| 2013/0250532 A1 | 9/2013 | Bryzek et al. |
| 2013/0273693 A1 | 10/2013 | Haba et al. |
| 2013/0299924 A1 | 11/2013 | Weber et al. |
| 2014/0014480 A1 | 1/2014 | Anderson et al. |
| 2014/0026649 A1 | 1/2014 | O'Donnell et al. |
| 2014/0034104 A1 | 2/2014 | O'Donnell et al. |
| 2014/0035630 A1 | 2/2014 | O'Donnell et al. |
| 2014/0044297 A1 | 2/2014 | Loeppert et al. |
| 2014/0103540 A1 | 4/2014 | Ching et al. |
| 2014/0162393 A1 | 6/2014 | Yang |
| 2014/0197042 A1 | 7/2014 | Zhang et al. |
| 2014/0221929 A1* | 8/2014 | Kamen ................. F04B 43/09 604/151 |
| 2014/0233782 A1 | 8/2014 | Bolognia et al. |
| 2014/0250975 A1 | 9/2014 | Kane |
| 2014/0311905 A1 | 10/2014 | Stetter et al. |
| 2015/0005709 A1* | 1/2015 | Pang ................. A61M 5/14586 604/151 |
| 2015/0010191 A1 | 1/2015 | Baumhauer, Jr. et al. |
| 2015/0075257 A1 | 3/2015 | Paik et al. |
| 2015/0075258 A1 | 3/2015 | Paik et al. |
| 2015/0131248 A1 | 5/2015 | Dakhiya et al. |
| 2015/0177171 A1 | 6/2015 | Kim et al. |
| 2015/0198551 A1 | 7/2015 | Jun et al. |
| 2015/0247818 A1 | 9/2015 | Silvester et al. |
| 2015/0362451 A1 | 12/2015 | Hunziker et al. |
| 2016/0047774 A1 | 2/2016 | Teysseyre et al. |
| 2016/0105737 A1 | 4/2016 | Kierse et al. |
| 2016/0193407 A1* | 7/2016 | Qin ................... A61M 5/14586 604/506 |
| 2017/0131230 A1 | 5/2017 | Papageorge et al. |
| 2017/0232189 A1 | 8/2017 | Qin et al. |
| 2017/0257687 A1 | 9/2017 | Kierse et al. |
| 2017/0336343 A1 | 11/2017 | Bhat et al. |
| 2018/0050486 A1 | 2/2018 | Talgorn et al. |
| 2018/0059044 A1 | 3/2018 | Berduque et al. |
| 2018/0266984 A1* | 9/2018 | Pratt ................... G01N 27/4071 |
| 2018/0372675 A1 | 12/2018 | Wade et al. |
| 2019/0126018 A1 | 5/2019 | Browd et al. |
| 2019/0135614 A1 | 5/2019 | Kierse et al. |
| 2019/0184095 A1 | 6/2019 | Kim et al. |
| 2019/0227024 A1 | 7/2019 | Bhat et al. |
| 2019/0227026 A1 | 7/2019 | Bhat et al. |
| 2019/0255254 A1 | 8/2019 | Wilmont et al. |
| 2020/0411398 A1* | 12/2020 | Bolognia ................ H01L 23/20 |
| 2021/0148852 A1 | 5/2021 | Bolognia et al. |
| 2021/0196884 A1 | 7/2021 | Kim et al. |
| 2021/0322681 A1 | 10/2021 | Bolognia et al. |

FOREIGN PATENT DOCUMENTS

| | | |
|---|---|---|
| CN | 101409279 | 4/2009 |
| CN | 201490184 | 5/2010 |
| EP | 0015322 | 9/1980 |
| EP | 1732215 | 12/2006 |
| EP | 2086015 | 8/2009 |
| EP | 2765410 A1 | 8/2014 |
| EP | 2857349 A3 | 5/2015 |
| EP | 3480590 A1 | 5/2019 |
| EP | 3616737 A2 | 3/2020 |
| GB | 1452104 | 10/1976 |
| JP | S60-012780 | 1/1985 |
| JP | 63-26569 | 2/1988 |
| JP | H04-152664 | 5/1992 |
| JP | H05-258925 | 10/1993 |
| JP | H10-051017 | 2/1998 |
| JP | 2002-111041 | 4/2002 |
| JP | 2002-246514 | 8/2002 |
| JP | 2004-207540 | 7/2004 |
| JP | 2004-349537 | 12/2004 |
| JP | 2005-283389 | 10/2005 |
| JP | 2005-353867 | 12/2005 |
| JP | 2006-245311 | 9/2006 |
| JP | 2006-344737 | 12/2006 |
| JP | 2006-352136 | 12/2006 |
| JP | 2007-103413 | 4/2007 |
| JP | 2007-234913 | 9/2007 |
| JP | 2008-017421 | 1/2008 |
| JP | 2008-173462 | 7/2008 |
| JP | 2009-081100 | 4/2009 |
| JP | 2009-081160 | 4/2009 |
| JP | 2009-200189 | 9/2009 |
| JP | 2010-087021 | 4/2010 |
| JP | 2010-251662 | 11/2010 |
| KR | 10-0537093 | 12/2005 |
| KR | 2006-0045375 | 5/2006 |
| KR | 2009-0117004 | 11/2009 |
| KR | 10-2010-0112699 | 10/2010 |
| WO | WO 95/13839 | 5/1995 |
| WO | WO 96/02438 A1 | 2/1996 |
| WO | WO 97/44707 | 11/1997 |
| WO | WO 00/19190 A1 | 4/2000 |
| WO | WO 2005/101476 | 10/2005 |
| WO | WO 2007/129787 A1 | 11/2007 |
| WO | WO 2010/053997 | 5/2010 |
| WO | WO 2010/100929 | 9/2010 |
| WO | WO 2010/117874 | 10/2010 |
| WO | WO 2010/136919 | 12/2010 |
| WO | WO 2011/103720 A1 | 9/2011 |
| WO | WO 2016/015028 A1 | 1/2016 |
| WO | WO 2016/163630 A1 | 10/2016 |

(56) References Cited

FOREIGN PATENT DOCUMENTS

WO  WO 2017/099963 A1  6/2017
WO  WO 2020/040519 A1  2/2020

OTHER PUBLICATIONS

Chait, "High-Volume Print Forming, HVPFTM A New Method for Manufacturing Large Volumes of Complex Metal-Ceramic and Hybrid Components," World Wide Web Address: eoplex.com/images/eoplex_whitepaper_hvpf.pdf, accessed Aug. 24, 2012.
Chait, "Solving 'The Last Milli-Mile' Problem in Vehicle Safety; The EoPlex Approach to Powering Wireless Tire Pressure Sensors," World Wide Web Address: eoplex.com/images/eoplex_whitepaper_tire.pdf, accessed Aug. 24, 2012.
Chinese Office Action dated Aug. 11, 2016 for Chinese Patent Application No. 201410454353.9, 3 pages.
Chinese Office Action dated Dec. 21, 2015 for Chinese Patent Application No. 201410454357.7, filed Sep. 9, 2014, 10 pages.
Chinese Office Action dated Dec. 28, 2015 for Chinese Patent Application No. 201410454354.3, filed Sep. 9, 2014. 5 pages.
Chinese Office Action dated Dec. 30, 2013 for Chinese Patent Application No. 201110433902.0, filed Dec. 22, 2011. 6 pages.
Chinese Office Action dated Feb. 3, 2016 for Chinese Patent Application No. 201410454358.1, filed Sep. 9, 2014.
Chinese Office Action dated Jul. 18, 2016 for Chinese Patent Application No. 201410454357.7, 5 pages.
Chinese Office Action dated Mar. 2, 2016 for Chinese Patent Application No. 201410454353.9, filed Sep. 9, 2014.
Chinese Office Action dated Sep. 13, 2016 for Chinese Patent Application No. 201410454354.3, 6 pages.
Chou, J., Chapter 2: Electrochemical Sensors, Hazardous Gas Monitors, 1000 McGraw-Hill, pp. 27-35.
Decision of Rejection dated Jan. 18, 2016 for Japanese Patent Application No. 2011-279492, 8 pages and 8 page translation.
E. Meng et al., "Polymer MEMS for Micro Fluid Delivery Systems", American Chemical Society (ACS) Polymer MEMS Symposia, New York, New York, USA, Sep. 2003. (two pages).
European Communication under Rule 63(1) dated Oct. 8, 2015 in European Patent Application No. 15 170 129.9, 3 pages.
European Office Action dated Jan. 18, 2016 for European Patent Application No. 11 192 789.3, 5 pages.
Extended European Search Report dated Mar. 26, 2012, in European Application No. 11192789.3.
Extended European Search Report issued in application No. 18204196.2 dated Feb. 13, 2019.
Extended European Search Report dated Mar. 17, 2016 for European Patent Application No. 15170129.9. 12 pages.
Extended Search Report dated May 8, 2015 in European Patent Application No. 15151494.0, 7 pages.
F. Roozeboom et al., "System-in-Package Integration of Passives using 3D Through-Silicon Vias", Solid State Technology, May 2008, vol. 51, No. 5, pp. 38-47.
H.B. Fan et al., "Prediction of Delamination in a Bi-material System based on Free-Edge Energy Evaluation", Proceedings of the 53rd IEEE Electronic Components and Technology Conference, May 2003, pp. 1160-1164.
Hagleitner, et al., "Smart single-chip gas sensor microsystem", Nature 414, Nov. 15, 2001, 3 pages.
Hosiden, "Guide for Electret Condenser Microphones," World Wide Web Address: es.co.th/schemetic/pdf/KUC.pdf, accessed Aug. 24, 2012.
Japanese Office Action dated Feb. 10, 2016 for Japanese Patent Application No. 2015-079984, filed Apr. 9, 2015, 4 pages and 4 page translation.
International Search Report and Written Opinion in International Application No. PCT/US2021/027412, dated Aug. 13, 2021.
International Search Report and Written Opinion, dated Aug. 8, 2018, in International Application No. PCT/EP2018/062505, 11 pages.
Japanese Office Action dated Feb. 2, 2015 for Japanese Patent Application No. 2011-279492, filed on Dec. 21, 2011. 3 pages, 3 page translation.
Japanese Office Action dated Feb. 26, 2013 for Japanese Patent Application No. 2011279492: filed Dec. 21, 2011. 3 pages, 3 page translation.
Japanese Office Action dated Jun. 29, 2015 for Japanese Patent Application No. 2015-079984, filed Apr. 9, 2015. 3 pages, 3 page translation.
Japanese Office Action dated Mar. 31, 2014 for Japanese Patent Application No. 2011-279492, filed Dec. 21, 2011. 3 pages, 3 page translation.
K. Wang et al., "Interfacial Shear Stress, Peeling Stress and Die Cracking Stress in Trilyaer Electronic Assemblies", IEEE 7th Intersociety Conference on Thermomechanical Phenomena in Electronic Systems, May 2000, vol. 2, pp. 56-64.
Kim, et al., "Hydrogel-Based Integrated Antenna-pH Sensor", IEEE Sensors Conference, 2007, pp. 695-698.
Korean Office Action dated Jun. 17, 2013 for Korean Patent Application No. 10-2011-0139346 filed Dec. 21, 2011. 6 pages, 6 page translation.
M. Berger, "Polymer Carpets—A New Class of Nanomaterials for NEMS and MEMS", Nanowerk, Sep. 2, 2010. (retrieved from http://www.nanowerk.com/spotlight/spotid=17875.php).
M. Duplessis et al., "Physical Implementation of 3D Integrated Solenoids within Silicon Substrate for Hybrid IC Applications", IEEE European Microwave Conference, Oct. 2009, pp. 1006-1009.
Maseeh, et al., "A Novel Silicon Micro Amperometric Gas Sensor", IEEE 1991, pp. 359-362.
Massachusetts Institute of Technology, "Funneling Solar Energy: Antenna Made of Carbon Nanotubes Could Make Photovoltaic Cells More Efficient", ScienceDaily, Sep. 13, 2010. (retrieved from http://www.sciencedaily.com/releases/2010/09/100912151548.htm).
Notice of Allowance dated Dec. 26, 2013 for Korean Patent Application No. 10-2011-0139346 filed Dec. 21, 2011. 2 pages, 1 page translation.
Office Action dated Jul. 3, 2015 for Chinese Application No. 201410454353.9, 4 pages.
Office Action dated Mar. 17, 2016 for Taiwanese Patent Application No. 103131989. 5 pages.
Open Music Labs, "Electret Microphones," World Wide Web Address: openmusiclabs.com/learning/sensors/electret-microphones/, accessed Aug. 24, 2012.
Search Report dated Nov. 30, 2015 in Taiwanese Patent Application No. 103131988, 4 pages (.
T.D. Moore, "Peeling Stress Analyzed for Resistance to Delamination—Application to Multiple Thin Films on a Thick Substrate", IEEE 9th Intersociety Conference on Thermomechanical Phenomena in Electronic Systems, Jun. 2004, vol. 2, pp. 330-335.
Rogren et al., "A High Performance and Cost Effective Molded Array Package Substrate," World Wide Web Address: eoplex.com/QFP_MR_White_Paper.pdf, accessed Aug. 24, 2012.
Taylor et al., "'Spatial Forming' A Three Dimensional Printing Process," World Wide Web Address: eoplex.com/images/eoplex_whitepaper_3dprinting.pdf, accessed Aug. 24, 2012.
Taiwanese Office Action dated Jul. 11, 2014 for Taiwanese Patent Application No. 100146568, filed on Dec. 15, 2011. 4 pages, 3 page translation.
Taiwanese Office Action dated Nov. 26, 2015 for Taiwan Patent Application No. 103131988, filed Sep. 16, 2014. 7 pages with translation.
Taiwanese Search Report dated Jun. 11, 2015 for Taiwanese Patent Application No. 104113577, filed Dec. 15, 2011, 1 page and 1 page translation.
Translation of Office Action dated Oct. 26, 2015 in Japanese Patent Application No. 2015-079984, 6 pages.
University of Southern California, "Graphene Organic Photovoltaics: Flexible Material Only a Few Atoms Thick May Offer Cheap Solar Power", ScienceDaily, Jul. 24, 2010. (retrieved from http://www.sciencedaily.com/releases/2010/07/100723095430.htm).

(56) References Cited

OTHER PUBLICATIONS

Website for Goldpoint pH Sensor orp202g-2 having 2014 copyright date, http://www.igpg.com.cn/Products/Online_pH_ORP_Sensor2/75.html (accessed Jun. 10, 2016).
Website related to Andose pH sensor Glass ORP/pH sensor, http://www.aliexpress.com/store/product/Glass-PH-sensor-PH-electrode-for-pipe-on-stallation-ph-G2008/1040787_32259217887.html (accessed Jun. 10, 2016).
Y. Luo et al., "An Improved Estimate for Thermal Stresses in Multi-Layer Assemblies", IEEE 11th Intersociety Conference on Thermal and Thermomechanical Phenomena in Electronic Systems, May 2008, pp. 842-852.
Zevenbergen, Marcel A.G. et al., "Electrochecmical sensing of ethylene employing a thin ionic-liquid layer," Analytical Chemistry, Aug. 15, 2011, vol. 83, No. 16, pp. 6300-6307.
Zevenbergen, Marcel A.G. et al., "Solid state pH and chloride sensor with microfluidic reference electrode," 2016 IEEE International Electron Devices Meeting (IEDM), Dec. 2, 2016, pp. 26.1.1-26.1.4.
Extended European Search Report issued in application No. 20206101.6 dated Apr. 30, 2021.
Kanellos, "How Do You Make a Fuel Cell? Print it," CNET News, World Wide Web Address: news.cnet.com/How-do-you-make-a-fuel-cell-Print-it/2100-1008_3-6078124.html?tag=sas.email; accessed Aug. 24, 2012.
Nie, et al., "An integrated flex-microfluidic-Si chip device towards sweat sensing applications," Sensors and Actuators B, May 2, 2016, vol. 227, pp. 427-437.

\* cited by examiner

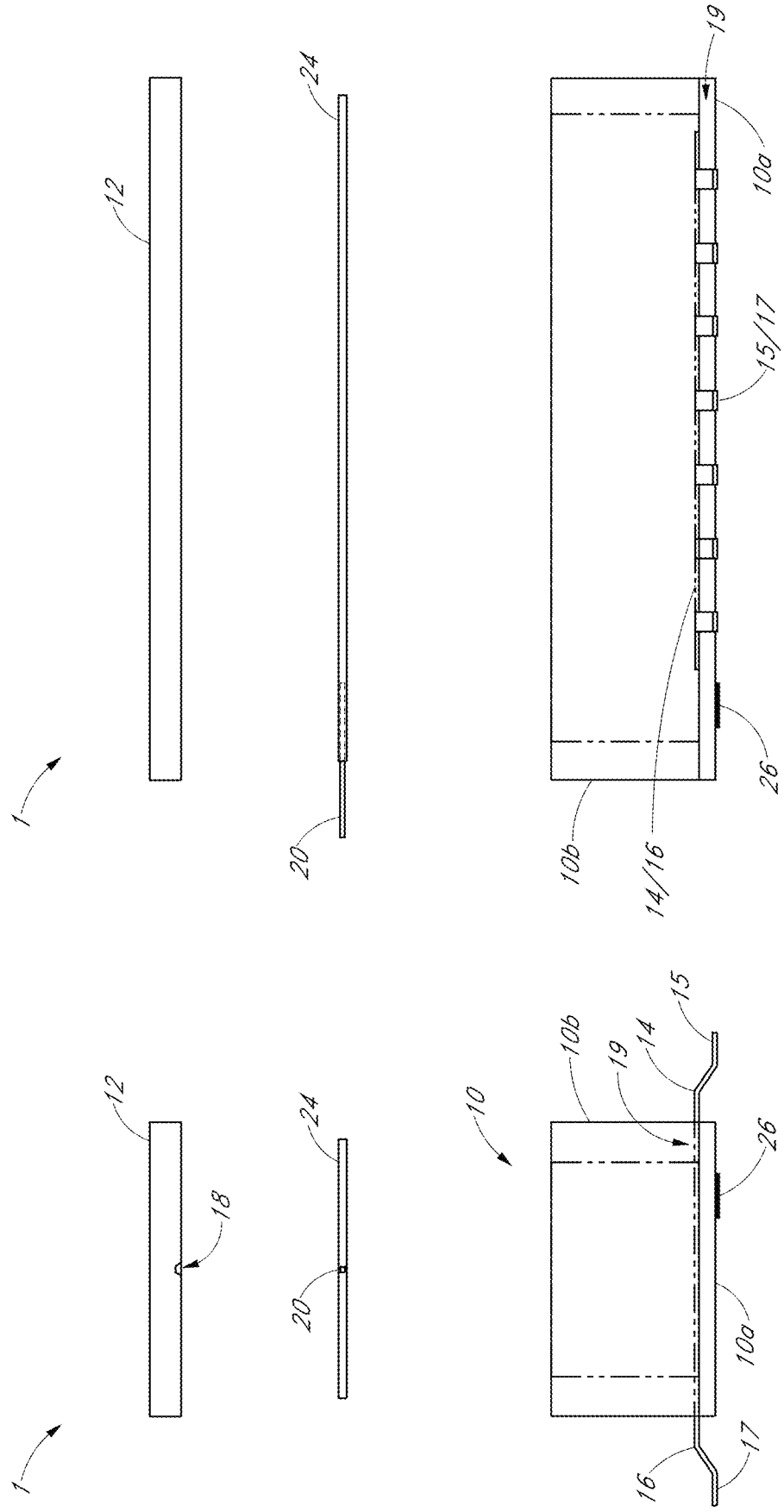

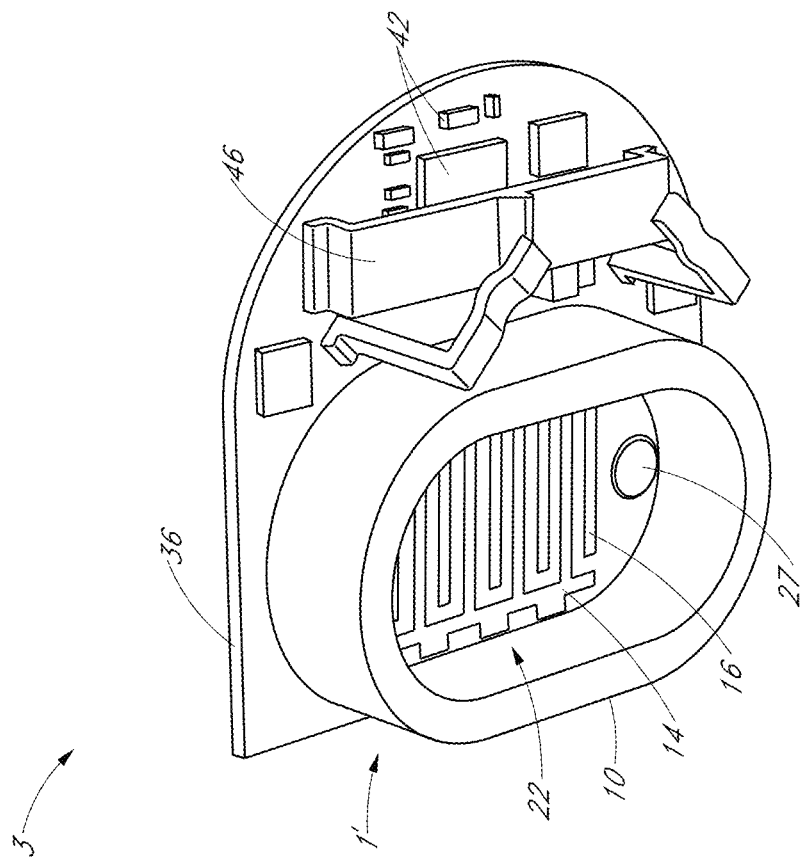
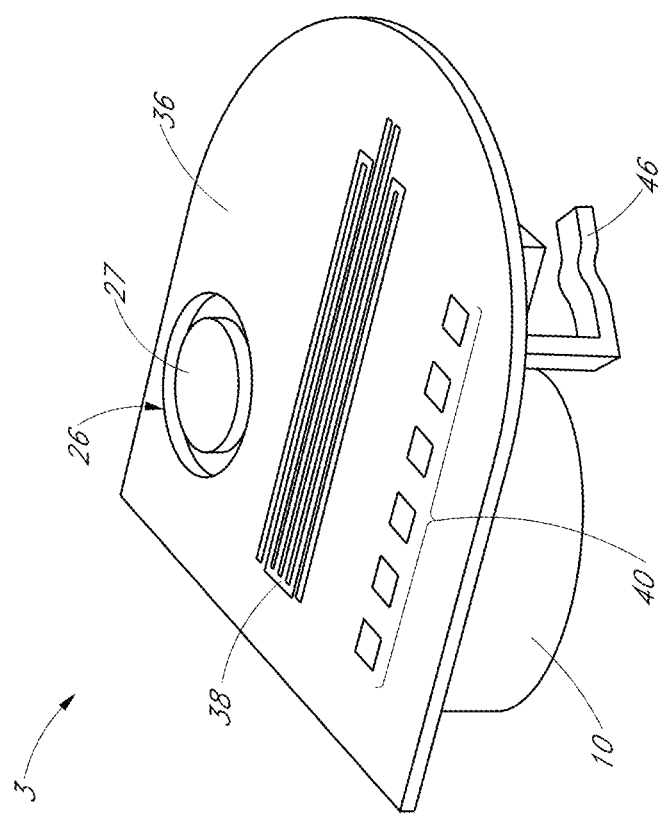

DEVICE WITH CHEMICAL REACTION CHAMBER

CROSS-REFERENCE TO RELATED APPLICATIONS

This application claims the benefit of U.S. Provisional Application No. 62/867,703 entitled "DEVICE WITH CHEMICAL REACTION CHAMBER," filed Jun. 27, 2019, the entire disclosure of which is incorporated herein by reference for all purposes. Further, this application is related to U.S. patent application Ser. No. 16/851,798, entitled "FLUID DELIVERY DEVICE," filed Apr. 17, 2020, the entire disclosure of which is incorporated herein by reference for all purposes.

BACKGROUND

Field

The field relates to devices including a chemical reaction chamber.

Description of the Related Art

Chemical reactions, such as electrolysis reactions in a closed chamber, can change the pressure in the chamber. The electrolysis reactions may occur when a potential difference or electrical current is applied to an electrolyte material, or due to a difference between the electropotentials of dissimilar materials (which may result in the generation of gas(es)). An electrolysis reaction system can include an electrolyte material disposed in a chamber, an anode electrode, and a cathode electrode.

SUMMARY

For purposes of summarizing the disclosure, certain aspects, advantages, and novel features of the innovations have been described herein. It is to be understood that not necessarily all such advantages can be achieved in accordance with any particular embodiment. Thus, the innovations described herein can be embodied or carried out in a manner that achieves or optimizes one advantage or group of advantages as taught herein without necessarily achieving other advantages as can be taught or suggested herein.

In one aspect, a device is disclosed. The device includes a housing that defines a chamber to be at least partially filled with an electrolyte material. The device also includes a plurality of electrodes that are at least partially embedded in the housing and exposed to the chamber. The device further includes an access port that provides fluid communication between an interior of the housing and the outside environs.

In one embodiment, the plurality of electrodes are at least partially embedded in a molding compound. The molding compound can at least partially define the housing.

In one embodiment, the device further includes a container that is disposed at least partially in the chamber. The container can be in fluid communication with the outside environs through the access port. The container can contain a substance. The substance can be configured to move through the access port in response to a pressure change caused by a chemical reaction within the chamber.

In one embodiment, the plurality of electrodes includes a portion of a patterned leadframe.

In one embodiment, the interior of the housing is configured to receive gas through the access port. The plurality of electrodes are configured to read out a voltage change in the electrolyte.

In one aspect, a device is disclosed. The device includes a chamber that is defined at least in part by a housing including a molding compound. The chamber is substantially sealed from the outside environs. The device also includes an electrolyte material that is disposed in the sealed chamber. The device also include a first electrode that is disposed in or on the housing. The first electrode is in contact with the electrolyte. The device further includes a second electrode that is disposed in or on the housing. The second electrode is in contact with the electrolyte. The chamber includes an access port that is configured to provide fluid communication between an interior of the housing and the outside environs.

In one embodiment, the molding compound includes a liquid crystal polymer.

In one embodiment, the housing includes a lid portion and a wall portion.

In one embodiment, the device further includes a container disposed at least partially in the chamber. The container can be configured to change shape in response to a change in pressure within the chamber. A substance contained in the container can be in physical communication with the outside environ through the access port. The substance can include a drug. The physical communication between the substance and the outside environ can be made through a conduit disposed at least partially in the access port.

In one embodiment, the device further includes a third electrode extending through a third portion of the liquid crystal polymer housing. The second electrode can be in contact with the electrolyte.

In one embodiment, the first electrode includes stainless steel.

In one aspect, an integrated device package is disclosed. The package includes a leadframe that is at least partially embedded in a molding material. The leadframe has a first electrode and a second electrode. The package also includes a chamber that is at least partially defined by the molding material. The chamber is configured to receive an electrolyte material. At least a portion of the leadframe is exposed to the chamber. The package further includes a reservoir that is separated from the chamber by way of a flexible film. The reservoir is configured to receive a fluid substance.

In one embodiment, at least a second portion of the leadframe is exposed on an outer surface of the molding material.

BRIEF DESCRIPTION OF THE DRAWINGS

FIG. 3 is a side view of the exploded view of the package illustrated in FIG. 2 as seen from one end.

FIG. 4 is another side view of the exploded view of the package illustrated in FIGS. 2 and 3, as seen from a different end.

FIG. 6A is a schematic top perspective view of the fluid delivery assembly illustrated in FIG. 5.

FIG. 6B is a schematic bottom perspective view of the fluid delivery assembly illustrated in FIG. 5.

DETAILED DESCRIPTION

Figure 1:
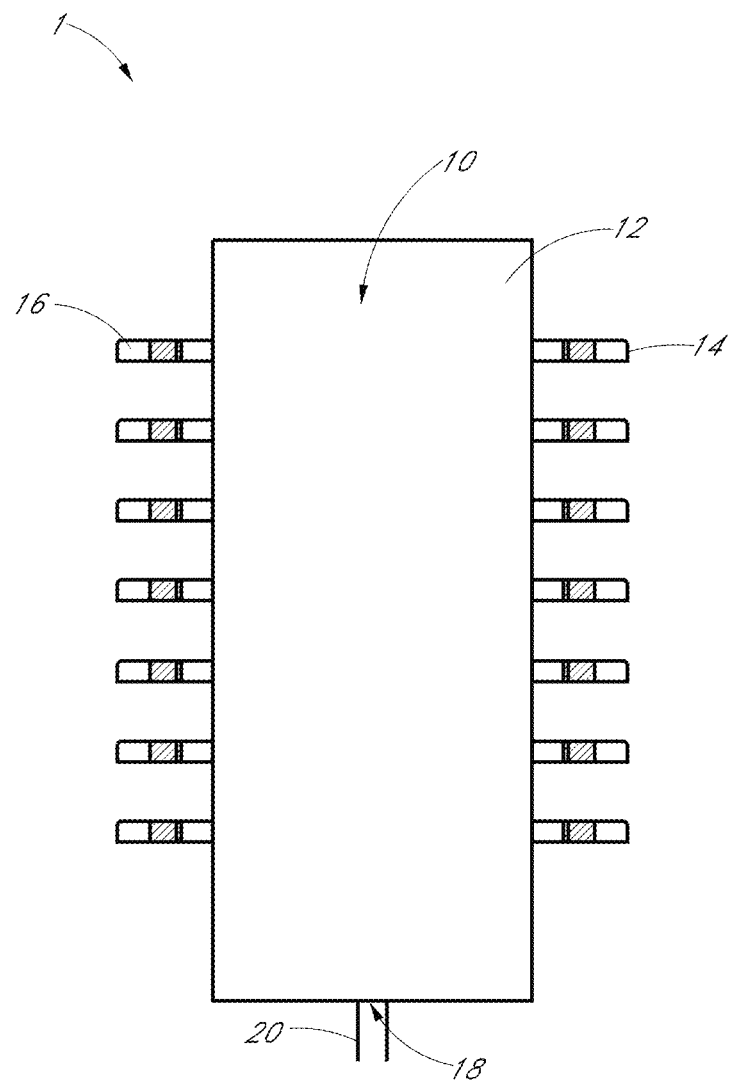
FIG. 1 is a top plan view of a package according to one embodiment.

Packages disclosed herein may be used for performing a chemical reaction that can be used to interact with external systems and media. For example, a package can include a chamber defined by a housing. A chemical reaction within the chamber can cause a pressure change in a substance (e.g., one or more liquids, gas, etc.) disposed in the chamber. Such a pressure change may be used, for example, to force out a substance though an access port formed on and/or in the housing. In some applications, the package can be used as a pump (e.g., an electrolysis pump for a drug delivery device). For example, voltage, current or a potential difference (e.g., a difference between the electropotential of dissimilar materials) can be applied to the chamber by way of electrodes (e.g., cathode and anode), thereby causing the chemical reaction in the chamber. The chemical reaction can change the pressure in the substance. The increased pressure in the fluid substance in the chamber can urge a material (such as a fluid drug) out through the access port. In some other applications, the package can be used as a sensor (e.g., a gas sensor) or a gas reference cell for calibration. For example, gas that comes into the chamber though the access port and a chemical in the chamber can cause a chemical reaction. The chemical reaction can change the voltage that is read out through the electrodes. Based on the voltage read out, the chemical structure of the gas can be determined.

A printed circuit board (PCB) with patterned electrodes formed therein and plastic walls can be glued together to form a package. However, typical PCB electrode materials (e.g., nickel, copper, etc.) may not be suitable for use as electrode materials for chemical reactions. Also, a typical PCB material may not effectively seal a chamber in the package. In certain applications, for example, the PCB materials can be subject to problems due to chemicals used during chemical reactions in the chamber. For example, solder mask, PCB electrode materials and/or PCB materials can be damaged by the chemicals. Further, gases (e.g., hydrogen, oxygen, carbon dioxide, etc.) produced in the chemical reaction can leak through the package. Such leakage may not be desirable when the package is used as, for example, an electrolysis pump package or a sensor package. For example, such leakage of gas may reduce the lifetime of an electrolysis pump used in the package, or degrade the accuracy of the sensor performance of a sensor used in the package.

In some aspects, a package is disclosed. The package can include a housing that defines a chamber. The housing can comprise a molded leadframe. The molded leadframe can comprise a plurality of leads or electrodes at least partially embedded in a molding compound, such as liquid crystal polymer (LCP), cyclic olefin copolymer (COC), polytetrafluoroethylene (PTFE), polyether ether ketone (PEEK), polyethylene terephthalate (PET), or the like material. The package with the LCP housing can provide better hermeticity as compared to a package with typical PCB materials. The molded leadframe can comprise a conductive material that defines an electrode or a lead for an electrical connection to the chamber. The molded leadframe that defines the chamber can be manufactured using typical leadframe manufacturing techniques.

FIG. 1 is a top plan view of a package 1 according to one embodiment. For example, the package 1 can be used as an electrolysis pump package, or an electrolysis sensor package. The package 1 can include a housing 10 that at least partially defines a chamber 22 (see FIG. 2), a first electrode 14, and a second electrode 16. During operation, a potential difference can be applied across the first and second electrodes 14, 16.

As illustrated in FIG. 1, the housing 10 can include a lid 12. In some embodiments, the housing 10 can be formed with a molding material such as liquid crystal polymer (LCP) or cyclic olefin copolymer (COC), thereby forming an insulating housing. The housing 10 can comprise a molded leadframe in which a metallic leadframe 19 is at least partially embedded (e.g., molded) into the molding material. In some embodiments, the housing 10 can include an access port 18. The access port 18 can comprise a hole through a portion of the housing 10. The access port 18 can provide physical communication between the chamber and the outside environs. A conduit 20 can be provided in the access port 18, in some embodiments. In some embodiments, the conduit 20 can convey fluid from package 1 to the outside environs. In other embodiments, the conduit 20 can convey fluid (e.g., liquid or gas) from the outside environs to within the package 1.

Figure 2:
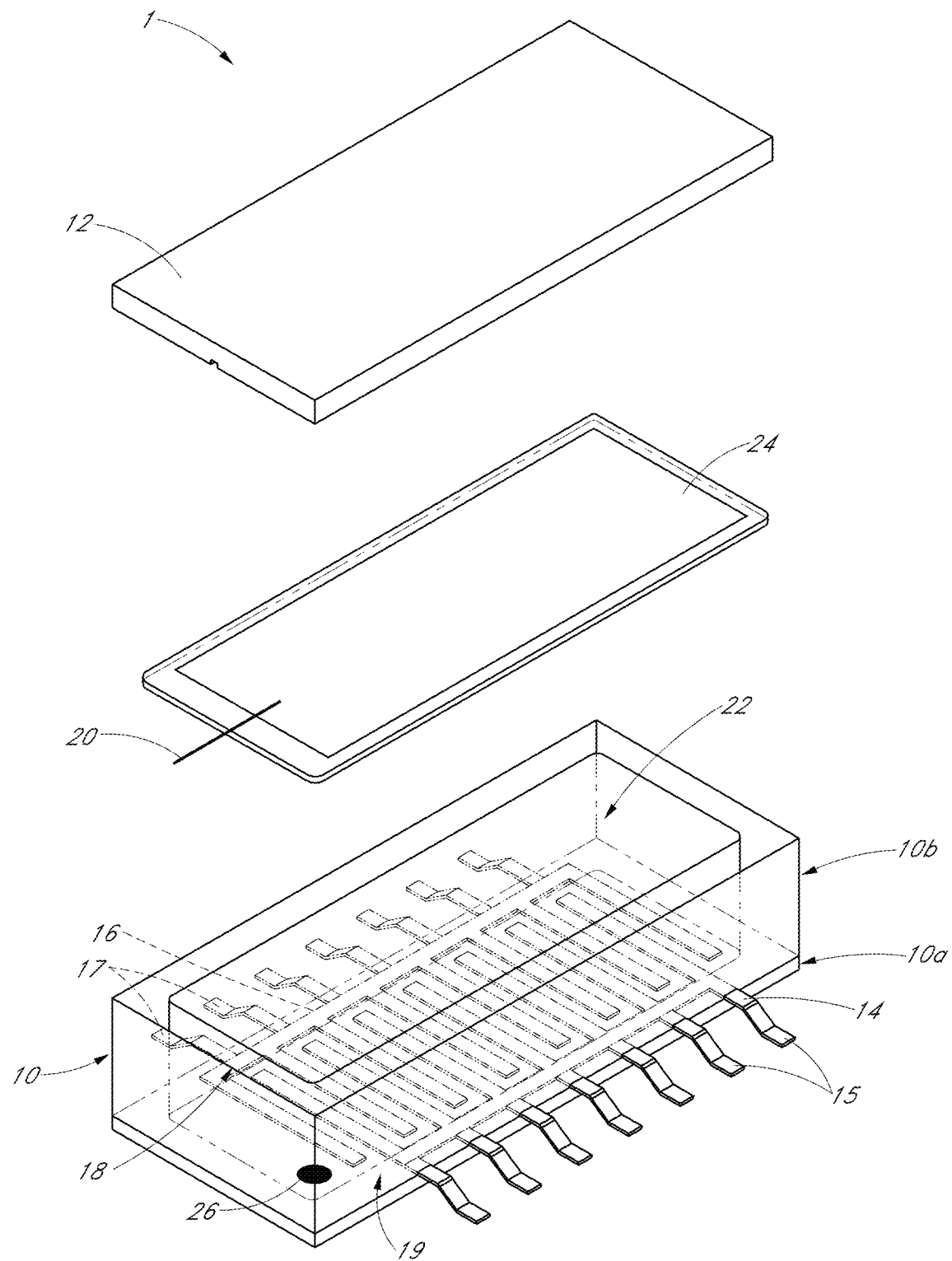
FIG. 2 is a perspective exploded view of the package illustrated in FIG. 1.
Figure 5:
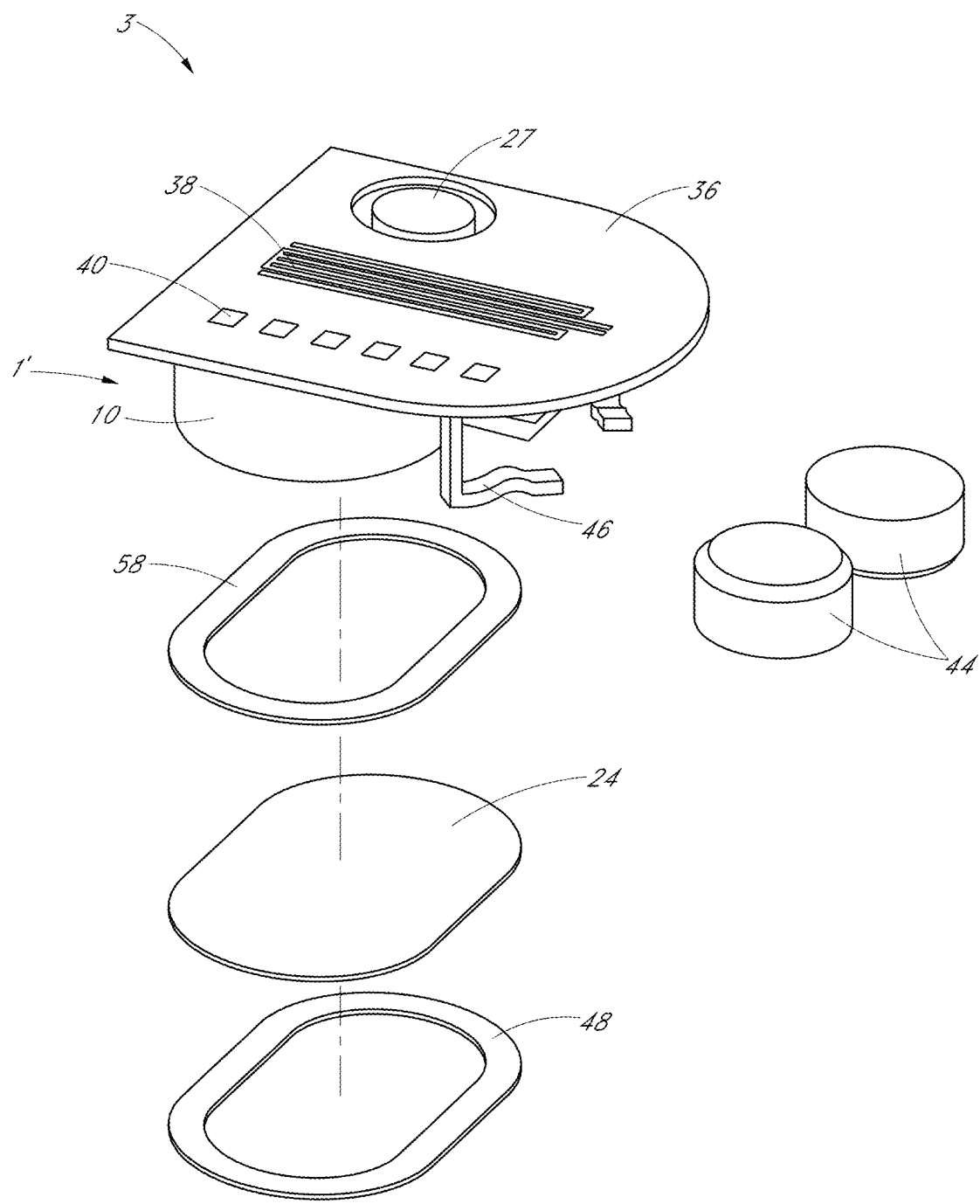
FIG. 5 is an exploded view of a fluid delivery assembly including a package according to one embodiment.

FIG. 2 is a perspective exploded view of the package 1 illustrated in FIG. 1. In FIG. 2, a chamber 22 defined by the housing 10 and a container 24 are illustrated. The chamber 22 of package 1 can be configured to receive an electrolyte material (not shown) for an electrolysis reaction. The container 24 can comprise a deformable material that can be squeezed or deformed under pressure that is applied to the container 24 by the electrolyte material in the chamber 22. As explained herein, the pressure of the electrolyte material can be increased and/or controlled by applying an electric potential to the electrolyte material by way of the electrodes 14, 16.

FIG. 3 is a side view of the exploded view of the package 1 illustrated in FIG. 2. FIG. 4 is another side view of the exploded view of the package 1 illustrated in FIGS. 2 and 3, as seen from a different side. Unless otherwise noted, the components of FIGS. 3 and 4 may be similar to or the same as like numbered components of FIGS. 1 and 2.

The illustrated housing 10 comprises a bottom portion 10a and a wall portion 10b that extends generally perpendicular to the bottom portion 10a. The bottom portion 10a and the wall portion 10b can be monolithically formed without an intervening bonding interface therebetween. For example, the bottom portion 10a and the wall portion 10b can be formed during a molding procedure. The molding procedure can embed the leadframe 19 into the molding compound and can also form the cavity 22. However, the housing 10 can comprise any suitable shapes.

The housing 10 can include a fill hole 26 through which the electrolyte material can be supplied to the chamber 22. After supplying the electrolyte material to the chamber 22, the fill hole 26 can be sealed, for example, with a plug. The illustrated housing 10 includes the sealed fill hole 26 at the bottom portion 10a of the housing 10. However, the sealed fill hole 26 may be formed at any position of the housing 10. In some embodiments, the sealed fill hole 26 may be omitted in arrangements in which the electrolyte material is supplied in another manner. The sealed fill hole 26 can be sealed after the electrolyte material is provided in the chamber 22 through the fill hole. In some embodiments, the sealed fill hole 26 can be sealed with the same material as the material used for the housing 10, e.g., a molding material.

The first and second electrodes 14, 16 can extend though portions of the housing 10 thereby providing respective first and second terminals 15, 17 extending outside of the chamber 22. The first and second electrodes 14, 16 can be at least partially embedded in the housing. The first and second electrodes 14, 16 can comprise any suitable material. In some embodiments, the first and second electrodes 14, 16 can comprise stainless steel. The first and second electrodes 14, 16 can be formed on and/or in the housing 10 using a leadframe manufacturing process. In some embodiments, a metal sheet (e.g., a copper sheet or a stainless steel sheet) can be patterned to form the leadframe 19 that includes the first and second electrodes 14, 16. For example, the first electrode 14 and/or the second electrode 16 can be embedded in the housing 10 by way of molding material. Therefore, the housing 10 can comprise a molded leadframe. The bottom portion 10a and the wall portion 10b of the housing 10 that comprises the molded leadframe can be formed as one piece, instead of two or more pieces bonded to one another.

The first and second electrodes 14, 16 can be formed on or at the bottom portion 10a of the housing 10. However, as long as the first and second electrodes 14, 16 are exposed to the chamber, the first and second electrodes 14, 16 can be formed anywhere in any suitable matter. In the illustrated embodiment, side surfaces of the leadframe 19 (e.g., side surfaces of the leads or terminals 15, 17) can be embedded in the molding compound, but the upper surfaces of the leads or terminal 15, 17 can be exposed to the chamber 22 and the electrolyte material. In some embodiments, lower surfaces of the leads or terminals 15, 17 can be embedded in the molding material but can extend outwardly through the molding material (e.g., FIG. 2) to electrically connect to an external device. In other embodiments, lower surfaces of the leads or terminals 15, 17 can be exposed through the molding material. For example, the first and second electrodes 14, 16 can be designed similarly to quad flat no-lead (QFN) packages at the bottom portion 10a of the housing 10, such that lower surfaces of the terminals 15, 17 are exposed through the molding material of the housing 10a to electrically connect to an external device. In some embodiments, the first and second terminals 15, 17 can have a half edged design.

The illustrated first and second electrodes 14, 16 are designed as interdigitated electrodes. However, the first and second electrodes 14, 16 may be formed in any other suitable matter. In some embodiments, there may be more electrodes formed in the package 1. For example, a third electrode, a fourth electrode, and/or more electrodes may be formed in the package 1. In some applications, the first electrode can be a positive electrode (e.g., anode), and the second electrode can be a negative electrode (e.g., cathode), or vice versa. In some embodiments, a third electrode can be included in the package 1. The third electrode can be used, for example, to monitor resistance from an electrode to another. A potential difference can be applied across the electrodes, which can induce a chemical reaction in the electrolysis in the chamber 22. The chemical reaction can increase the pressure of fluid (e.g., electrolyte material) in the chamber 22. As explained herein, the increased pressure of the electrolyte material can drive a fluid (such as a medication) out of the container 24.

The container 24 can be disposed anywhere in the chamber 22. The container 24 can contain therein a substance, such as a fluid substance (e.g., liquid or air). The substance can comprise, for example, a drug. In such embodiments, the drug contained in the container 24 can be forced out by increased pressure created by an electrolysis reaction in the chamber 22 though the conduit 20. For example, the conduit 20 can deliver the drug to a patient, or can be connected to another device which delivers the drug to the patient. The drug can be forced out at a rate controlled by the applied voltage though the first and second electrodes 14, 16.

When the package 1 is used as a sensor, the container 24 may be omitted. In such embodiments, a gas to be sensed can enter the chamber from the access port 18 and can react with the electrolyte material in the chamber 22. The reaction can induce a potential difference that can be detected by the first and second electrodes 14, 16 and by processing circuitry in electrical communication with the package 1). The detected voltage can be analyzed to identify the gas that enters the package 1.

In some embodiments, the container 24 may be provided on the top of the housing to seal the chamber 22. However, the material used for the container 24 may not be able to hermetically seal the chamber 22. The lid 12 can hermetically seal the chamber 22, thereby eliminating or mitigating gas leakage through the container 24. The lid can be coupled with the container 24 and/or the housing 10 in any suitable manner. In some embodiments, the lid 12 can be coupled with the container 24 and/or the housing 10 by way of a secondary epoxy. In some embodiments, the lid 12 can be coupled with the container 24 and/or the housing 10 by way of ultrasonic welding, or any other suitable manner. In some embodiments, the package can comprise a plurality of containers (not illustrated). For example, the plurality of containers can contain therein different contents (e.g., multiple drugs).

In some embodiments, the chamber 22 can be divided into a plurality of sub-chambers. For example, the housing 10 can be structured such that the chamber 22 comprises two separated sub-chambers. In such embodiments, each sub-chamber can have a container 24 and/or separate electrodes 14, 16. In some embodiments, different sub-chambers may have different pressures to controllably and/or selectably deliver the drug to the patient.

The package 1 illustrated in FIGS. 1-4 can be formed by providing a housing with electrodes and providing an electrolyte material in a chamber formed by the housing. The housing can comprise liquid crystal polymer (LCP) or cyclic olefin copolymer (COC). Using LCP or COC for the housing can provide a better resistance against chemicals, such as electrolyte material, and better moisture protection, as compared to a housing comprising other materials. Providing the housing can include forming an electrode on or at an inner surface of the housing. Providing the housing can include providing a container in the chamber. Providing the housing can include providing a lid to substantially seal the chamber from outside environ.

FIGS. 5-7B show various views of a fluid delivery assembly 3 including a package 1', according to various embodiments. Unless otherwise noted, components of FIGS. 5-7B may be the same as or generally similar to like-numbered components of FIGS. 1-4. A bottom cover or lid (or a housing assembly) (not shown) can cooperate with the housing 10 to define the chamber 22. A package substrate 36 (such as a printed circuit board, or PCB) can serve as an upper cover to close the chamber 22. In some embodiments, the package substrate 36 can be overmolded on the outside of the substrate 36 for protection and/or sealing. The package substrate 36 can provide electrical communication to an external device or system by way of contact pads 40. Moreover, as shown in FIG. 6A, an antenna 38 can be formed on an outer surface of the package substrate 36 to provide wireless communication with an external device. For example, information regarding a user's health and/or about the package 1' itself can be transmitted to a computing device, such as a mobile device (such as a smartphone), a computer server, or any other type of computing device.

As shown, a plug 27 (such as a T-shaped plug) can be provided to plug the fill hole 26 after electrolyte is delivered to the chamber 22. A fluid (such as a drug or any other suitable liquid) can be delivered to a cavity of the container 24. As with the embodiment of FIGS. 1-4, a conduit or fluid outlet can be provided to deliver fluid to the user. For example, a conduit or other device can be connected to the fluid outlet to deliver the fluid to the patient.

As shown in FIG. 6B, the fluid delivery assembly 3 can include one or more batteries 44 to power the devices 42. The batteries 44 can be secured to the package substrate 36 by way of one or more corresponding clips 46. One or more electronic devices 42 can be connected to the substrate 36. The electronic device(s) 42 can comprise any suitable type of devices, such as integrated circuit die(s), passive electronic device(s) (e.g., capacitors, resistors, inductors, etc.), accelerometer(s), sensor die(s), etc. For example, in embodiments in which the package 1' is configured to deliver a fluid substance (e.g., a drug) to a patient, the electronic device(s) 42 can comprise circuitry configured to drive the electrodes 14, 16 for dispensing a drug through the conduit 20 and to the patient. In embodiments in which the package 1' is configured as a sensor (e.g., to detect or sense a gas), the electronic device(s) 42 can be programmed to process signals transduced by the electrodes 14, 16 to identify the detected gas. In some embodiments, the electronic devices 42 can comprise a wireless communication device. The wireless communication device can include an antenna and/or a filter. In some embodiments, the electronic devices 42 can include a motion sensor. The motion sensor can include an accelerometer and/or a rotation sensor. A first seal 48 can seal a rim of the container 24 to the cover or other structure that encloses the chamber 22. A second seal 58 can be provided to seal the rim of the container 24 to the housing 10.

Figure 7B:
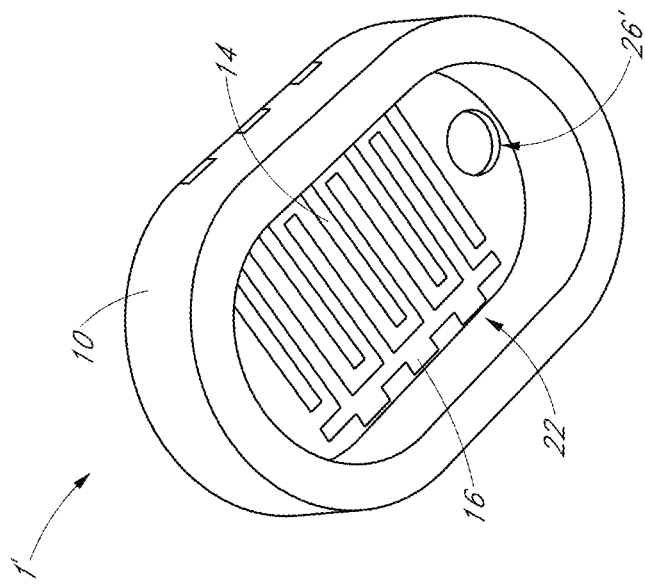
FIG. 7B is a schematic top perspective view of the package illustrated in FIG. 5.
Figure 7A:
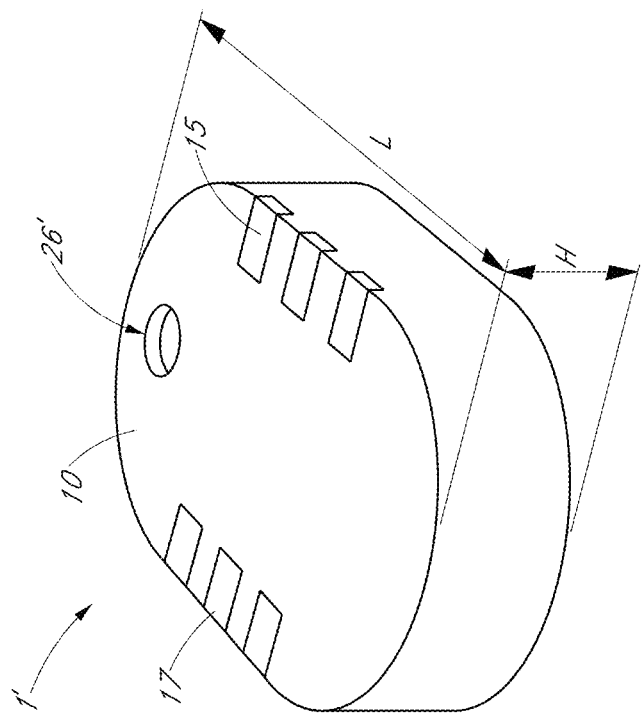
FIG. 7A is a schematic bottom perspective view of the package illustrated in FIG. 5.

Referring to FIG. 7A, the package 1' has a package height H and a package length L. In some embodiments, the package height H can be in a range of, for example, 2 mm to 10 mm, in a range from, for example, 2 mm to 7 mm, in a range from, for example, 5 mm to 10 mm, or in a range from, for example, 4 mm to 7 mm. In some embodiments, the package length L can be in a range from, for example, 10 mm to 30 mm, in a range from, for example, 10 mm to 20 mm, in a range from, for example, 15 mm to 30 mm, or in a range from, for example, 15 mm to 20 mm.

Figure 8A:
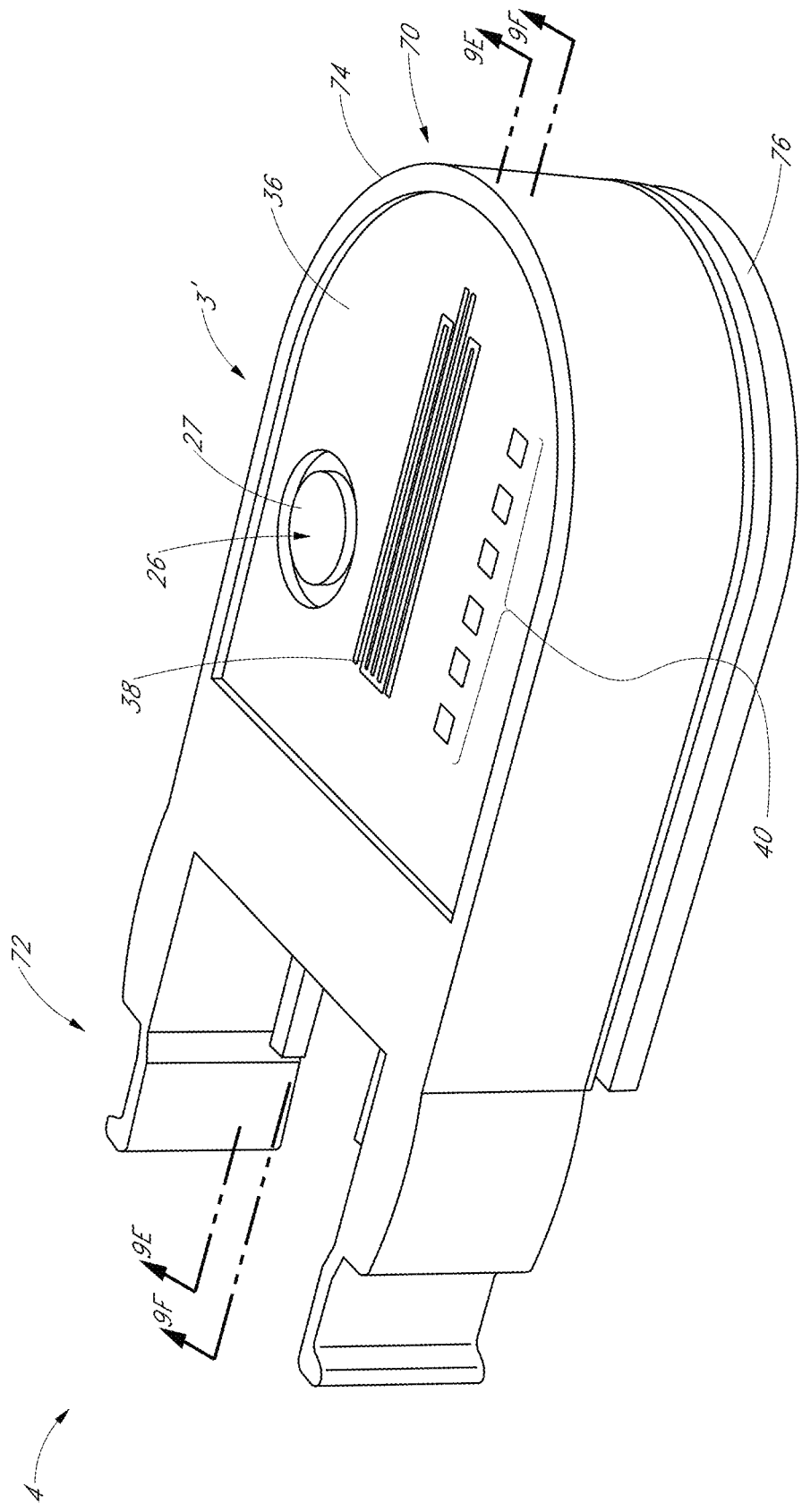
FIG. 8A is a top schematic perspective view of a fluid delivery device according to one embodiment.
Figure 8B:
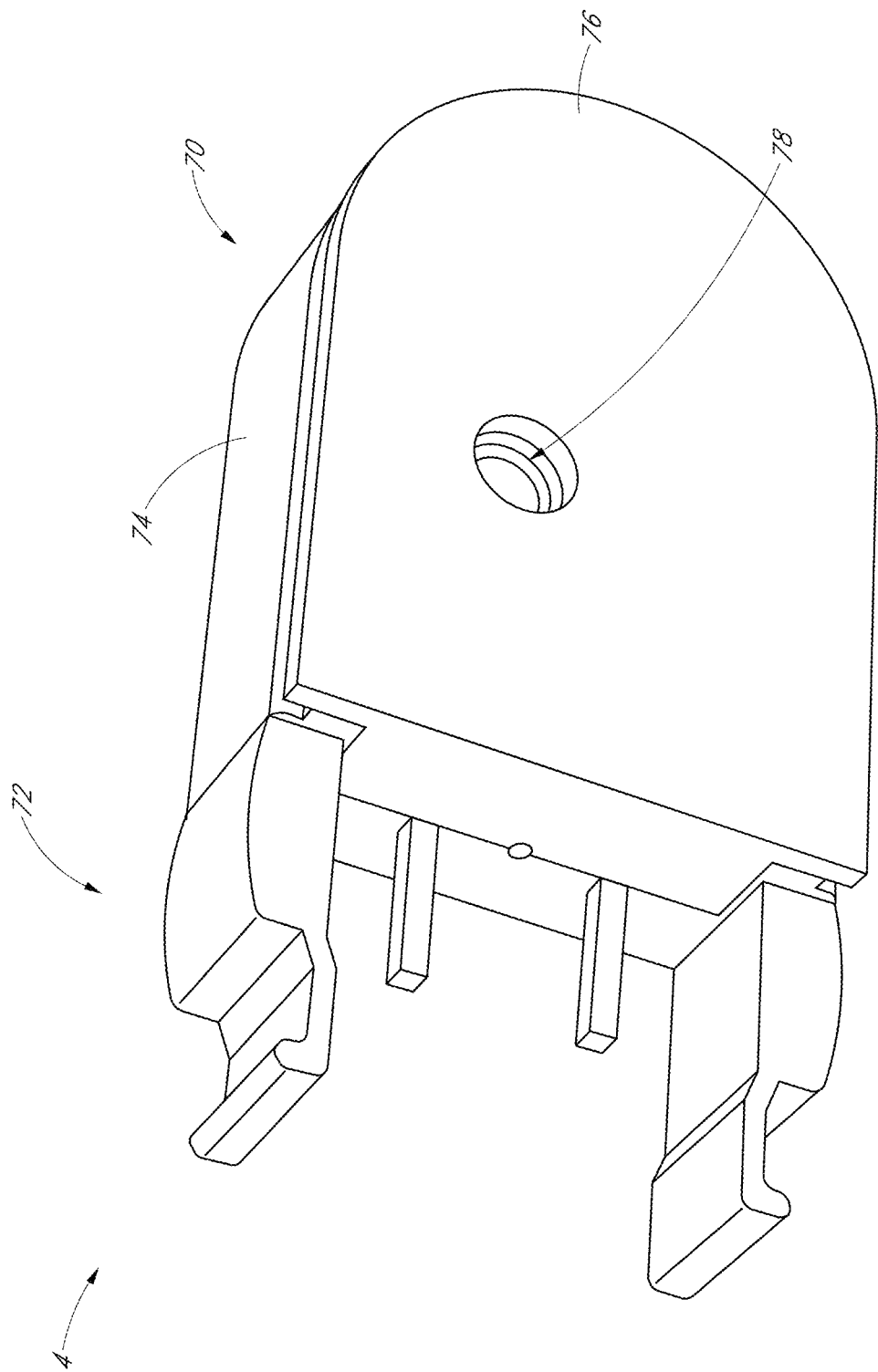
FIG. 8B is a bottom schematic perspective view of the fluid delivery device illustrated in FIG. 8A.
Figure 8C:
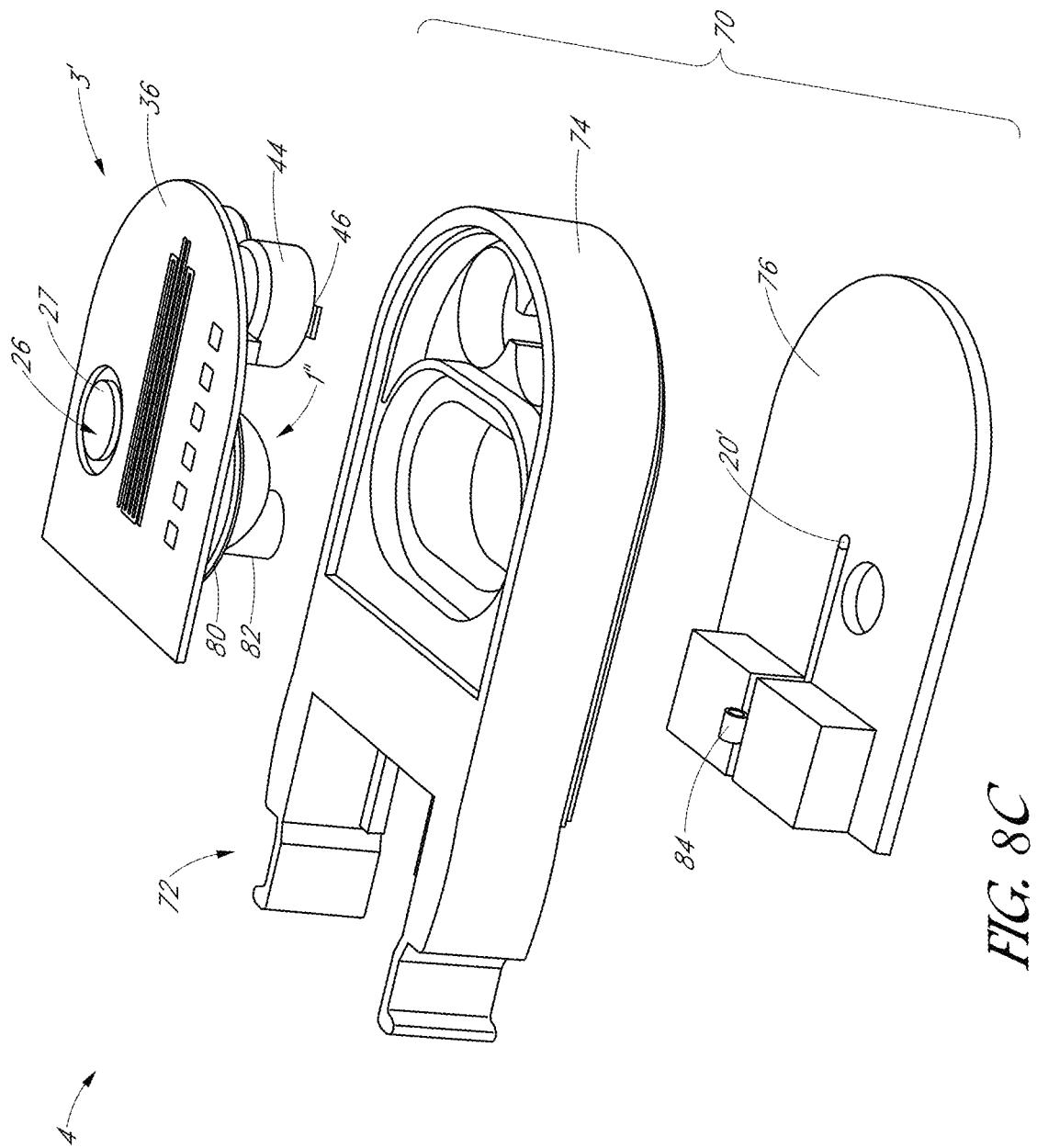
FIG. 8C is a schematic top exploded view of the fluid delivery device illustrated in FIGS. 8A and 8B.
Figure 8D:
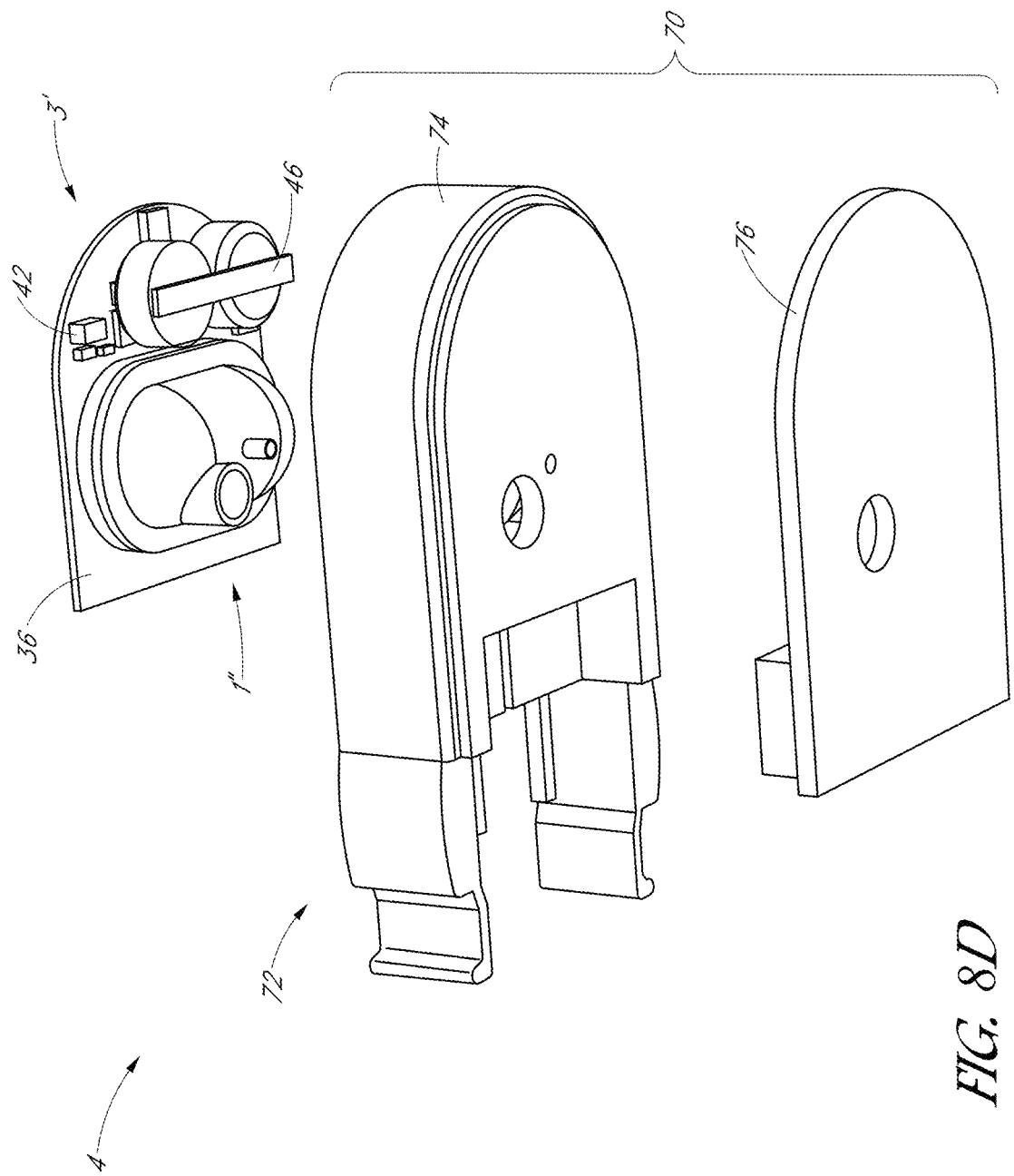
FIG. 8D is a schematic bottom exploded view of the fluid delivery device illustrated in FIGS. 8A-8C.
Figure 8E:
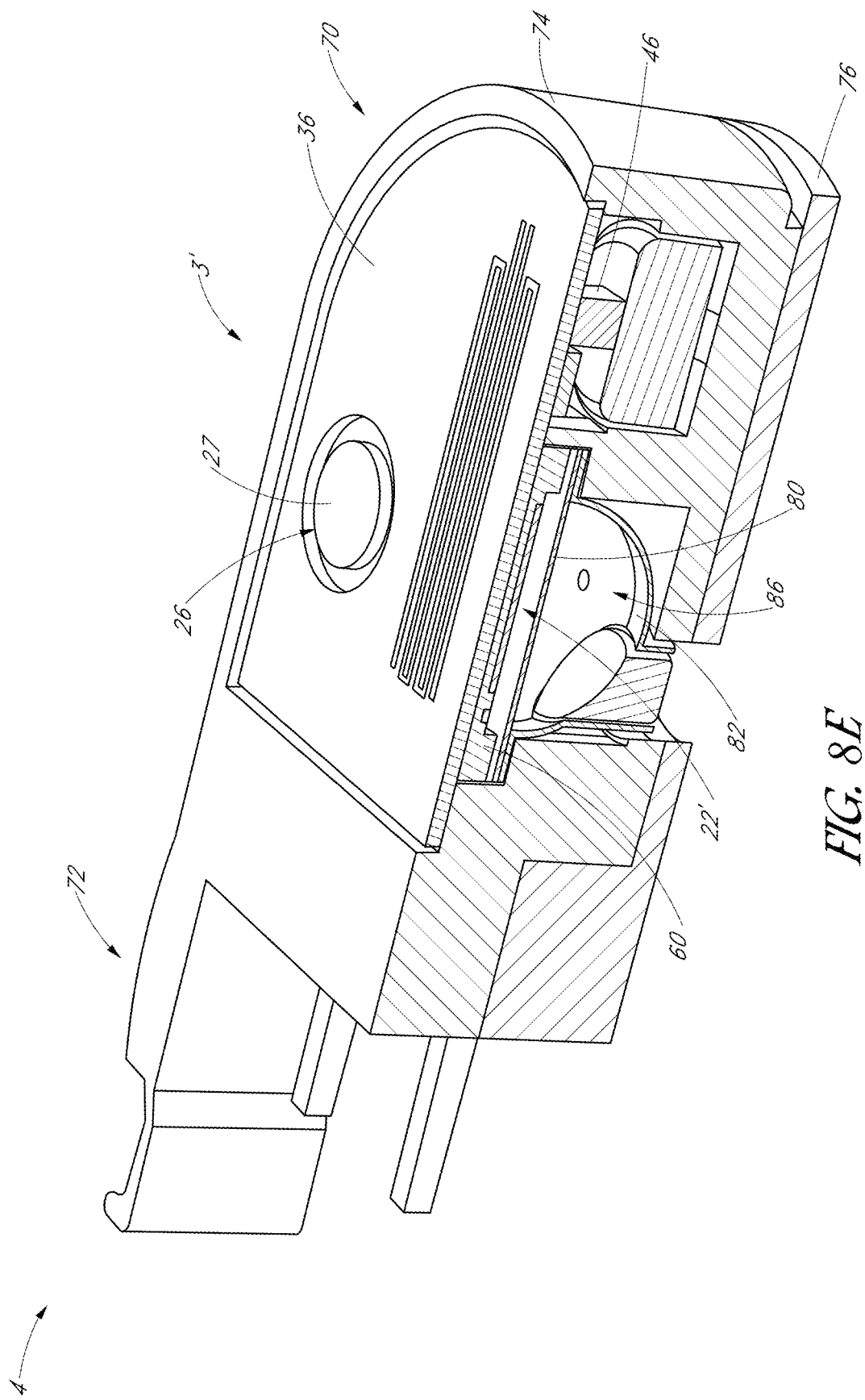
FIG. 8E illustrates a schematic cross section of the fluid delivery device illustrated in FIGS. 8A-8D.
Figure 8F:
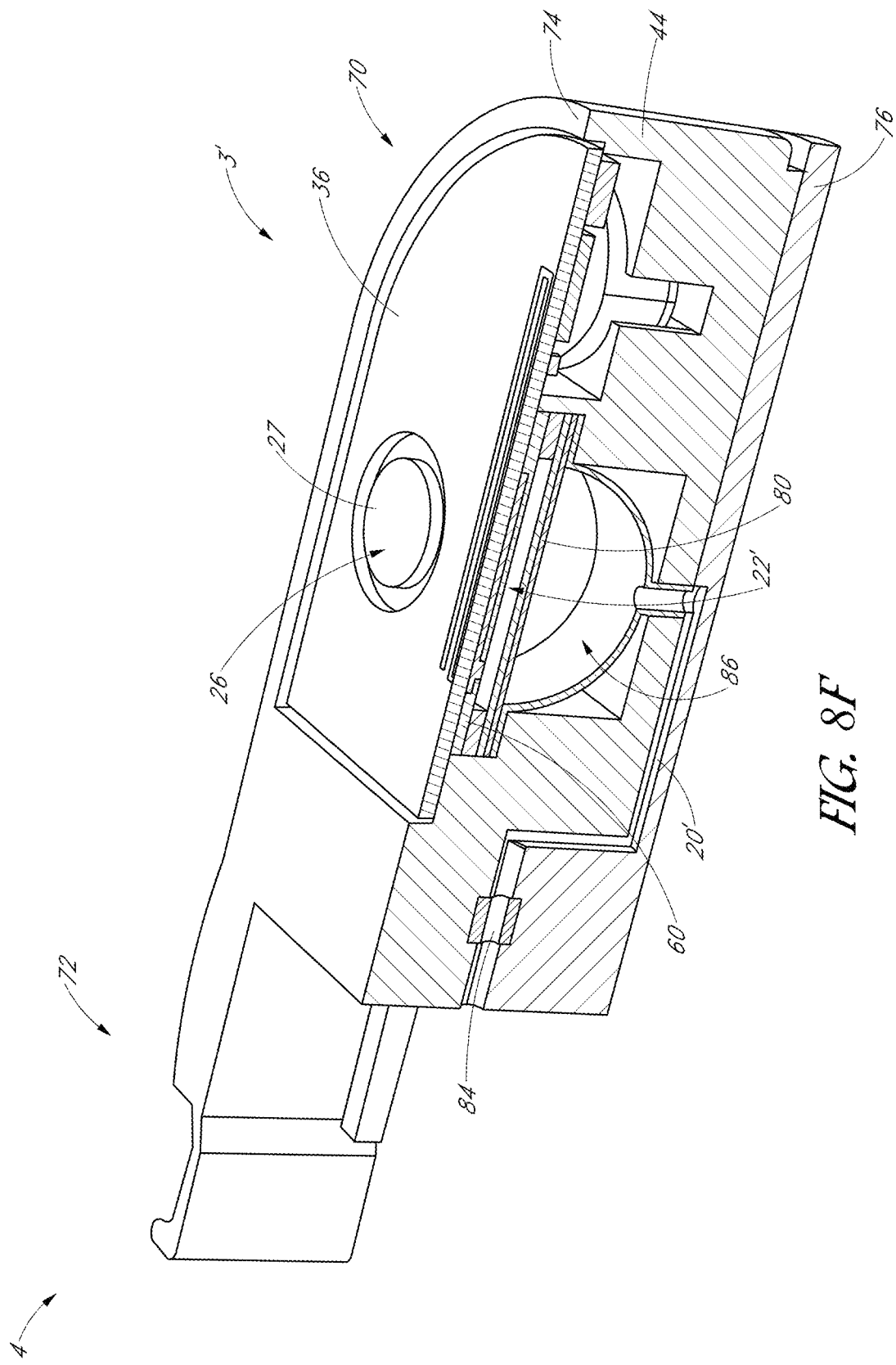
FIG. 8F illustrates a schematic cross section of the fluid delivery device illustrated in FIGS. 8A-8E.

FIGS. 8A-8F illustrates various views of a fluid delivery device 4 according to one embodiment. FIG. 8A is a top schematic perspective view of the fluid delivery device 4. FIG. 8B is a bottom schematic perspective view of the fluid delivery device 4. FIG. 8C is a schematic top exploded view of the fluid delivery device 4. FIG. 8D is a schematic bottom exploded view of the fluid delivery device 4. FIG. 8E illustrates a schematic cross section of the fluid delivery device 4 illustrated in FIG. 8A. FIG. 8F illustrates a schematic cross section of the fluid delivery device 4 illustrated in FIG. 8A. Unless otherwise noted, components of FIGS. 8A-8F may be the same as or generally similar to like-numbered components of FIGS. 1-7B. The fluid delivery device 4 can include a fluid delivery assembly 3' and a casing 70 that at least partially encases the fluid delivery assembly 3'. The casing 70 comprises a connector 72, an upper portion 74 and a lower portion 76. The upper portion 74 of the casing 70 can be shaped to receive the fluid delivery assembly 3'.

The fluid delivery assembly 3' can be generally similar to the fluid delivery assembly 3 illustrated in FIGS. 6A and 6B. However, instead of the package 1' of fluid delivery system 3, the fluid delivery system 3' comprises a package 1" (see FIGS. 8C and 8D). The package 1" can comprise the molded leadframe 60 that at least partially defines a chamber 22' for receiving an electrolyte material, a membrane 82 for receiving a substance, and an inflatable film 80. In some applications, the substance can comprise a fluid substance (e.g., liquid or air). The substance can comprise, for example, a drug. The substance can be provided in the membrane 82 through a hole 78.

The inflatable film 80 can be inflatable during manufacture and during use. During manufacture, the inflatable film 80 can inflate in response to injection of an electrolyte material into the chamber 22'. The electrolyte material can be disposed in the chamber 22' between the inflatable film 80 and the molded leadframe 60. A fill hole 26 can be sealed with a plug 27 after the electrolyte material is provided in the chamber 22' through the fill hole 26. During use, the inflatable film 80 can inflate in response to reaction of the electrolyte material in the chamber 22' and the first and second electrodes 14, 16. In some embodiments, the substance in the reservoir 86 can be forced out from the reservoir 86 in response to the reaction.

The casing 70 can comprise a conduit 20'. The conduit 20' can be defined at least partially in the lower portion 76 of the casing 70. In some embodiments, the conduit 20' can convey the substance from the reservoir 86 to the outside environs. In other embodiments, the conduit 20' can convey substance (e.g., liquid or gas) from the outside environs to within the reservoir 86.

In some embodiments, the connector 72 of the casing 70 can be connected to a structure, such as an external device. For example, the structure can be a wearable device. In some applications, the connector 72 can comprise a clip for connecting the fluid delivery device 4 to the external device. The external device can comprise a needle assembly that allows communication between the fluid delivery device 4 and a patient's body (e.g., inside a patient's vasculature).

The fluid delivery device 4 can also include a check valve 84. The check valve 84 can be positioned in the conduit 20'. In some embodiments, the check valve can mitigate or prevent the substance from moving in a direction. In some embodiments, the check valve 84 can comprise a sensing elements (e.g., an optical sensor). In some embodiments, the check valve 84 can monitor pressure and/or leakage of the substance through the conduit 20'.

In some embodiments, the fluid delivery device 4 can comprise a sensor (not illustrated). The sensor can comprise an accelerometer. The accelerometer can be coupled to a switch (not illustrated) that is electrically coupled to the battery 44. Before an initial use of the fluid delivery device 4, the battery 44 may not be electrically coupled to the first and second electrodes 14, 16 or one or more electronic devices 42 mounted on the package substrate 36. When the accelerometer detects an acceleration greater than a threshold acceleration, the switch can electrically couple the battery 44 to the first and second electrodes 14, 16 or one or more electronic devices 42. In such embodiments, the sensor can minimize drain of current from the battery 44 prior to use of the fluid delivery device 4.

Although disclosed in the context of certain embodiments and examples, it will be understood by those skilled in the art that the present invention extends beyond the specifically disclosed embodiments to other alternative embodiments and/or uses and obvious modifications and equivalents thereof. In addition, while several variations have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the present disclosure. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the aspects that follow.

What is claimed is:

1. A device comprising:
   a housing defining a chamber configured to receive an electrolyte material, the housing at least partially defined by a molding compound;
   a conductive leadframe patterned to include a plurality of electrodes and a plurality of terminals, the plurality of electrodes at least partially embedded in the molding compound and exposed to the chamber, the plurality of terminals configured to electrically connect the plurality of electrodes to an external device; and
   an access port that is configured to provide fluid communication between an interior of the housing and the outside environs.

2. The device of claim 1, wherein the molding compound comprises liquid crystal polymer (LCP), cyclic olefin copolymer (COC), polytetrafluoroethylene (PTFE), polyether ether ketone (PEEK), or polyethylene terephthalate (PET).

3. The device of claim 2, wherein the patterned, conductive leadframe comprises a molded leadframe, with the plurality of terminals at least partially embedded in the molding compound and exposed at an outer surface of the molding compound.

4. The device of claim 1, further comprising a container disposed at least partially in the chamber, the container is configured as to be in fluid communication with the outside environs through the access port.

5. The device of claim 4, wherein the container contains a substance, the substance is configured to move through the access port in response to a pressure change caused by a chemical reaction within the chamber.

6. The device of claim 1, wherein the interior of the housing is configured to receive gas through the access port.

7. The device of claim 6, wherein the plurality of electrodes are configured to read out a voltage change in the electrolyte material.

8. A device comprising:
   a chamber defined at least in part by a housing comprising a molding compound, the chamber being substantially sealed from the outside environs;
   an electrolyte material disposed in the sealed chamber;
   a first electrode disposed in or on the housing, the first electrode in contact with the electrolyte;
   a second electrode disposed in or on the housing, the second electrode in contact with the electrolyte;
   a first terminal configured to electrically connect the first electrode to an external device;
   a second terminal configured to electrically connect the second electrode to the external device,
   wherein the chamber comprises an access port that is configured to provide fluid communication between an interior of the housing and the outside environs; and
   a container disposed at least partially in the chamber, wherein the container is configured to change shape in response to a change in pressure within the chamber.

9. The device of claim 8, wherein the molding compound comprises a liquid crystal polymer.

10. The device of claim 8, wherein the housing comprises a lid portion and a wall portion.

11. The device of claim 8, wherein a substance contained in the container is in physical communication with the outside environs through the access port.

12. The device of claim 11, wherein the substance comprises a drug.

13. The device of claim 11, wherein a conduit disposed at least partially in the access port provides the physical communication between the substance and the outside environs.

14. The device of claim 8, further comprising a third electrode extending through a portion of the housing, the third electrode in contact with the electrolyte.

15. The device of claim 8, wherein the first electrode comprises stainless steel.

16. An integrated device package comprising:
   a leadframe at least partially embedded in a molding material, the leadframe having a first electrode, a second electrode, a first terminal configured to electrically connect the first electrode to an external device, and a second terminal configured to electrically connect the second electrode to the external device;
   a chamber at least partially defined by the molding material, the chamber configured to receive an electrolyte material, at least a portion of the leadframe exposed to the chamber; and
   a reservoir separated from the chamber by way of a flexible film, the reservoir configured to receive a fluid substance.

17. The package of claim 16, wherein at least a second portion of the leadframe is exposed on an outer surface of the molding material, the second portion including at least one of the first and second terminals.

18. A device comprising:
   a chamber defined at least in part by a housing comprising a molding compound, the chamber being substantially sealed from the outside environs;
   an electrolyte material disposed in the sealed chamber;
   a first electrode disposed in or on the housing, the first electrode in contact with the electrolyte;
   a second electrode disposed in or on the housing, the second electrode in contact with the electrolyte;
   a first terminal configured to electrically connect the first electrode to an external device;

a second terminal configured to electrically connect the second electrode to the external device, wherein the chamber comprises an access port that is configured to provide fluid communication between an interior of the housing and the outside environs; and a container disposed at least partially in the chamber, wherein a substance contained in the container is in physical communication with the outside environs through the access port.

19. The device of claim 18, wherein the substance comprises a drug.

20. The device of claim 18, wherein a conduit disposed at least partially in the access port provides the physical communication between the substance and the outside environs.

* * * * *